(12) United States Patent
Higgins et al.

(10) Patent No.: US 10,092,705 B2
(45) Date of Patent: Oct. 9, 2018

(54) INJECTION DEVICE

(71) Applicant: Sanofi, Paris (FR)

(72) Inventors: Daniel David Higgins, Bristol (GB); Joseph Butler, Rugby Warwickshire (GB); David Aubrey Plumptre, Worcestershire (GB); Matthew Jones, Warwick (GB)

(73) Assignee: Sanofi, Paris (FR)

( * ) Notice: Subject to any disclaimer, the term of this patent is extended or adjusted under 35 U.S.C. 154(b) by 116 days.

(21) Appl. No.: 14/783,156

(22) PCT Filed: Apr. 8, 2014

(86) PCT No.: PCT/EP2014/056995
§ 371 (c)(1),
(2) Date: Oct. 8, 2015

(87) PCT Pub. No.: WO2014/166913
PCT Pub. Date: Oct. 16, 2014

(65) Prior Publication Data
US 2016/0051767 A1 Feb. 25, 2016

(30) Foreign Application Priority Data
Apr. 10, 2013 (EP) .................................. 13163100

(51) Int. Cl.
*A61M 5/315* (2006.01)
*A61M 5/31* (2006.01)

(52) U.S. Cl.
CPC .... *A61M 5/31586* (2013.01); *A61M 5/31511* (2013.01); *A61M 5/31553* (2013.01);
(Continued)

(58) Field of Classification Search
CPC .......... A61M 5/31586; A61M 5/61511; A61M 5/31553; A61M 2005/3126;
(Continued)

(56) References Cited

U.S. PATENT DOCUMENTS

2008/0147005 A1* 6/2008 Moller .............. A61M 5/14566
604/134
2008/0243087 A1* 10/2008 Enggaard .......... A61M 5/31553
604/208

(Continued)

FOREIGN PATENT DOCUMENTS

CN 101227943 7/2008
CN 101641126 2/2010
(Continued)

OTHER PUBLICATIONS

Clock spring definition.*

(Continued)

*Primary Examiner* — Nathan R Price
*Assistant Examiner* — Dung Ulsh
(74) *Attorney, Agent, or Firm* — Fish & Richardson P.C.

(57) ABSTRACT

The invention refers to an injection device comprising a housing (10), containing a cartridge (170) with an amount of liquid to be dispensed, a drive sleeve (41), which is rotationally constrained to the housing (10) during dose setting and spring driven rotatable relative to the housing (10) during dose dispensing, a dose dial member (60) for setting a dose to be dispensed, which is rotatable relative to the housing (10) during dose setting and during dose dispensing, and which is rotationally coupled to the drive sleeve (41) during dose dispensing. The device further comprises a last dose protection mechanism (41, 50, 60) for preventing the setting of a dose, which exceeds the amount of liquid left in the cartridge (170), with a limiter (50), which is interposed (Continued)

between the drive sleeve (41) and the dose dial member (60). Further, the device comprises two different display members (110, 120), each indicating the set dose.

13 Claims, 5 Drawing Sheets

(52) U.S. Cl.
CPC ....... *A61M 5/3155* (2013.01); *A61M 5/31533* (2013.01); *A61M 5/31535* (2013.01); *A61M 5/31541* (2013.01); *A61M 5/31548* (2013.01); *A61M 5/31558* (2013.01); *A61M 5/31565* (2013.01); *A61M 5/31568* (2013.01); *A61M 2005/3126* (2013.01); *A61M 2005/3152* (2013.01); *A61M 2005/3154* (2013.01)

(58) Field of Classification Search
CPC ............ A61M 5/3152; A61M 5/31533; A61M 5/31535; A61M 5/3154; A61M 5/31541; A61M 5/31548; A61M 5/3155; A61M 5/31558; A61M 5/31565; A61M 5/31568; A61M 2005/3154
See application file for complete search history.

(56) References Cited

U.S. PATENT DOCUMENTS

| | | | |
|---|---|---|---|
| 2009/0247951 A1* | 10/2009 | Kohlbrenner | A61M 5/20 604/134 |
| 2010/0114025 A1 | 5/2010 | Moeller | |
| 2010/0274198 A1* | 10/2010 | Bechtold | A61M 5/31551 604/189 |
| 2011/0054412 A1 | 3/2011 | Eich et al. | |
| 2012/0245532 A1* | 9/2012 | Frantz | A61M 5/31551 604/211 |
| 2015/0352288 A1* | 12/2015 | Andersen | A61M 5/20 604/134 |

FOREIGN PATENT DOCUMENTS

| | | |
|---|---|---|
| CN | 102014991 | 4/2011 |
| EP | 0 730 876 | 9/1996 |
| EP | 1 804 858 | 10/2009 |
| EP | 1 909 870 | 3/2011 |
| WO | WO 2004/078241 | 9/2004 |
| WO | WO 2005/018721 | 3/2005 |
| WO | WO 2007/017052 | 2/2007 |
| WO | WO 2008/145171 | 12/2008 |
| WO | WO 2012/049139 | 4/2012 |

OTHER PUBLICATIONS

Rote Liste, "50. Hypophyses-, Hypothalamushormone, andere regulatorische Peptide u. ihre Hemmstoffe," Chapter 50, ed. 2008, 20 pages.

International Preliminary Report on Patentability in International Application No. PCT/EP2014/056995, dated Oct. 13, 2015, 6 pages.

International Search Report and Written Opinion in International Application No. PCT/EP2014/056995, dated May 9, 2014, 10 pages.

* cited by examiner

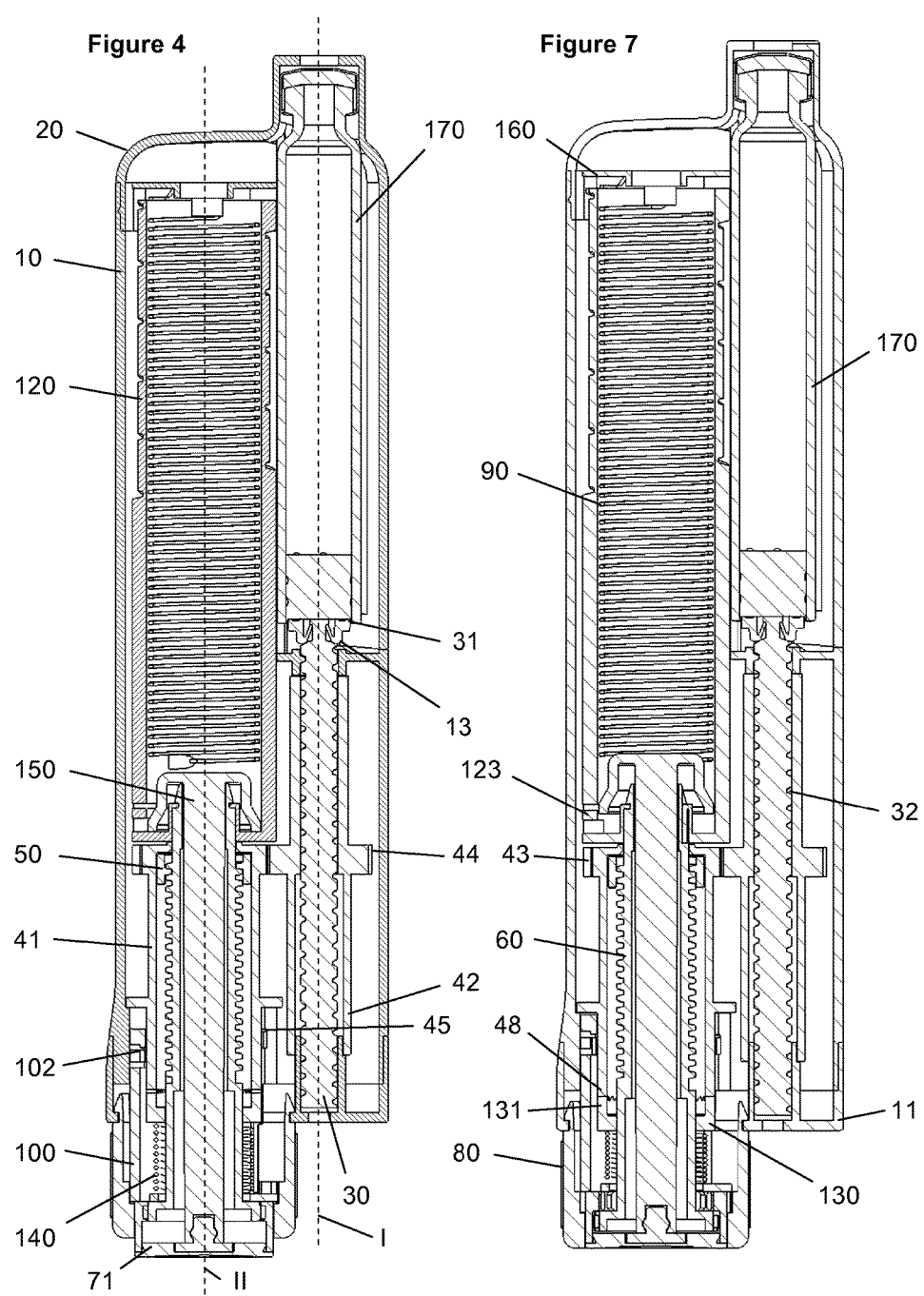

INJECTION DEVICE

CROSS-REFERENCE TO RELATED APPLICATIONS

This application is a U.S. national stage application under 35 USC § 371 of International Application No. PCT/EP2014/056995, filed on Apr. 8, 2014, which claims priority to European Patent Application No. 13163100.4, filed on Apr. 10, 2013, the entire contents of which are incorporated herein by reference.

The present invention is generally directed to an injection device, i.e. a drug delivery device for selecting and dispensing a number of user variable doses of a medicament.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present invention is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting. In general, the present invention is applicable for all of these types of devices, i.e. for devices with or without a drive spring.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. The remaining dose in the cartridge is indicated to the user by the position of the bung and the distal end of the piston rod within the cartridge. Especially visually impaired users may find it difficult to identify the remaining dose in the cartridge.

Further, EP 1 804 858 B1 discloses an injection device which comprises a housing, a resilient member and a dose setting member operatively connected to a dose indicator barrel positioned within the housing. The resilient member is a helical spring adapted to provide a force in the axial direction of the injection device, the force being necessary for ejecting a dose from the injection device. The dose setting member and the dose indicator barrel are movable relative to each other and cooperate to set the dose to be ejected from the injection device. The dose indicator barrel engages a threaded portion of the housing. The dose indicator barrel, during dose setting, is adapted to undergo a combined rotational and translational movement within the housing and relative to the housing. The combined rotational and translational movement of the dose indicator barrel is caused by its threaded interface with the housing. Generally, a translational movement of a dose indicator barrel during dose setting either results in the indicator barrel protruding from the housing depending on the amount of the set dose or this requires a relatively long housing, if it is preferred that the barrel is covered within the housing independent of the set dose.

WO 2008/145171 A1 discloses an injection device which requires a manual force necessary for ejecting a dose from the injection device, i.e. without the aid of a spring or the like. This device comprises a housing, a first component for pressing out the injection liquid from a container and a dosing component in threaded engagement with the first component. The dosing component can rotate together with the first component relative to the housing for the purpose of selecting a desired injection dosing. Further, the dosing component is in threaded engagement with a window sleeve which moves axially within the housing and relative to the dosing component upon rotation of the dosing component. A number scale provided on the dosing component is visible through this window sleeve. A knob is provided, which is rotated during dose setting and which is simultaneously axially moved away from the housing as the window sleeve translates out of the housing during dose setting. Thus, although the dosing component does not perform a translational movement during dose setting, there is still a component (knob with window sleeve) protruding from the housing when a dose is set.

In addition, a drive mechanism including a torsion spring is known from EP 1 909 870 B1. This device comprises a limiter which is coupled to a driver and a piston rod such that relative rotation between the driver and the piston rod during dose setting causes the limiter to move towards a stopping position wherein the limiter prevents setting of a dose which exceeds the amount of a medicament in a reservoir in the injection device. As the piston rod has a small diameter compared with the driver and the torsion spring, limiting actuation of the device and thus withstanding a relatively high torque via the piston rod may be difficult in some cases.

It is an object of the present invention to provide a drug delivery device requiring low dispensing forces applied by the user and an improved indication of the set doses. Especially, it is an object of the present invention to provide an injection device with a reliable mechanism which prevents the setting of a dose exceeding a predefined threshold, e.g. the amount of medicament left in a cartridge of the injection device. It is a further object to make the drug delivery device compact in size, preferably without components translating out of the housing during dose setting.

This object is solved by a device as defined in claim 1.

According to a first embodiment of the present invention the injection device comprises a housing containing a cartridge with an amount of liquid to be dispensed, a, preferably sleeve-like, drive member, which is rotationally constrained to the housing during dose setting and spring driven in rotation relative to the housing during dose dispensing, a dose dial member for setting a dose to be dispensed, which is rotatable relative to the housing during dose setting and during dose dispensing, and which is rotationally coupled to the drive member during dose dispensing. The device further comprises a last dose protection mechanism for preventing the setting of a dose, which exceeds the amount of liquid left in the cartridge, with a limiter, which is interposed between the drive member and the dose dial member. Further, the device may comprise two different display members, each indicating the set dose.

Thus, as the drive member is coupled to the housing, for example via a first clutch, and the dose dial member is rotated during dose setting, and preferably also during dose cancelling, the limiter may be coupled to the drive member and the dose dial member such that the limiter is moved with respect to these members. On the other hand, if, for example by a second clutch, any relative rotation between the dose dial member and the drive member is prevented during dose dispensing, the limiter will maintain its position with respect to the drive member and the dial member. This results in the position of the limiter corresponding to the total amount of set doses, i.e. the sum of all set and dispensed doses plus the actually set and not yet dispensed dose. An end stop may be provided at a position which allows abutment or interaction of the limiter and an end stop of the dose dial member or the drive member as soon as a predefined threshold is reached. Typically, this may be a maximum settable dose, e.g. the amount of medicament left in a cartridge of the injection device. If the limiter abuts such an end stop, no further relative rotation between the dose dial member and the drive member is possible. Thus, the drive mechanism and the injection device may be blocked to prevent setting of a higher or further dose and/or to prevent dose dispensing. According to a preferred embodiment, abutment of the limiter at an end stop prevents setting of a dose which exceeds the amount of a medicament in a cartridge in the injection device but allows dispensing the actually set dose. In this respect, the limiter may comprise a rotational stop and the dose dial member may comprise a corresponding counter stop, which abut if a dose is set, which exceeds the amount of liquid left in a cartridge.

The general function of a drive mechanism as defined above is to set a dose and to subsequently dispense the set dose. Dose setting (dose dialing) usually requires a user to manipulate one element of the drive mechanism, preferably to rotate a dose dial member e.g. via a dial grip. During dose dispensing the dose dial member may move, e.g. rotate, back to its original position wherein a drive member, which is not actuated during dose setting is moved together with the dose dial member during dose dispensing. The movement of the drive member may be a rotation, a displacement or a combined movement e.g. along a helical path. The drive member may act on a lead screw which functions as a piston rod for expelling medicament from a cartridge during dose dispensing.

In addition to this basic function of a drive mechanism it is in some cases preferred to allow a cancelling of an already set dose, i.e. a correction or a deselecting of a dose. Preferably the user simply has to rotate the dose dial member, e.g. via a dial grip, in the opposite direction compared to the rotation during dose setting. Preferably, the drive member is not actuated during dose resetting, either.

To allow rotation of components of the mechanism, it is preferred if the components are mainly located concentrically about a common longitudinal axis of the drive mechanism in the injection device. Thus, the components may have a tubular or sleeve-like shape. For example, the limiter, the drive member and the dose dial may each be a tubular element with the limiter surrounding the dose dial member and the drive member surrounding the limiter (and thus the dose dial member). As an example, the limiter may be a nut or may be designed as a half-nut, i.e. a ring segment. Preferably, the last dose protection mechanism comprises a nut member as the limiter, which is rotationally constrained to the drive member, e.g. a drive sleeve, and in threaded engagement with the dose dial member.

Further, although it is desirable to reduce the total number of components of a drive mechanism, it might be useful for manufacturing reasons to split one or more components into separate elements. For example, the housing may comprise an outer body and an insert and/or an inner body which is axially and/or rotationally constrained to the outer body. In addition, a clutch may be designed by providing protrusions and/or recesses directly on the components which are to be coupled or decoupled by the clutch. As an alternative, a separate clutch element may be provided interposed between the two components which have to be coupled or decoupled.

The device of the present invention has the benefit of not only limiting the set dose as a safety feature to avoid setting of a dose which exceeds the amount of medication left in the cartridge, but additionally displaying the set dose in two different ways. In general, various displays are known, for example an electronic (e.g. LCD) display, a sleeve or drum with numbers or symbols printed on the outside, which are visible through a window or are highlighted by a marker. On the one hand, patients using injection devices need to know exactly the set dose to avoid overdosage or underdosage, on the other hand, patients are often visually impaired which makes it difficult to identify the set dose. Providing two different displays allows displaying to the user the set dose and further displaying a rough indication of the magnitude or range of the set dose. According to a preferred embodiment of the invention, the device comprises a number sleeve as one of the display members and a sliding gauge element as the second display member. The number sleeve may display every single dose unit or every other unit, while the gauge element may comprise a symbol or a colour coding to indicate the magnitude or range of the set dose. For example, different colours or different markings on the gauge element may be visible depending from the set dose. Further, the gauge feature is particularly useful in an auto-injector, where no other major visual clues are provided to the user about the dose magnitude.

Preferably, the housing has a first aperture or window. The display members may comprise a dose indicator, which is positioned within the housing and rotatable relative to the housing during dose setting and during dose dispensing, and a gauge element, which is interposed between the housing and the dose indicator, and which is axially guided within the housing and in threaded engagement with the dose indicator such that rotation of the dose indicator causes an axial displacement of the gauge element. A second aperture or window may be provided in the gauge element, which is positioned with respect to the first aperture or window of the housing such that at least a part of the dose indicator is visible through the first and second apertures or windows.

A reliable way of ensuring that the dose indicator displays the actually set dose is to permanently rotationally constrain the dose dial member to the dose indicator. Thus, rotation of the dose dial member during dose setting, dose correction and dose dispensing is transferred to the dose indicator.

Preferably, the dose indicator is a number sleeve having a series of numbers or symbols arranged on a helical line on its outer surface. Thus, rotation of the number sleeve allows displaying different dose units. The gauge element preferably has a distal part located on the distal side of the second aperture or window and a proximal part located on the proximal side of the second aperture or window. An indication of the magnitude of the set dose may be given, for example by the distal part and the proximal part having a different outer surface, like different colours, different symbols or markings.

To dispense a set dose, a piston rod may be used pushing a bung or the like of the cartridge in the distal direction. It is preferred if the piston rod is coupled to the drive member, e.g. a drive sleeve, with the piston rod being rotationally constrained to the housing during dose setting and allowing it to rotate during dose dispensing. The piston rod may be a lead screw in threaded engagement with the housing, such that rotation of the piston rod results in an axial movement of the piston rod relative to the housing. Thus, preventing rotation of the piston rod during dose setting, for example via the drive member, prevents unintended axial movement of the piston rod during dose setting.

The injection device may comprise a ratchet clutch, which is arranged between the drive member and the dose dial member, and which allows relative rotation of the drive sleeve and the dose dial member during dose setting and which rotationally constrains the drive sleeve to the dose dial member during dose dispensing. Preferably, this clutch is activated by pushing a dose button, a trigger, or the like, against the force of a spring, which biases the clutch in its dose setting position.

Although the general concepts of the last dose mechanism and the two display members are not limited to spring driven devices, the injection device preferably comprises a spring for driving the drive member. According to an embodiment, the drive sleeve is coupled to a torsion spring during dose dispensing, which is strained during dose setting. This coupling may be an indirect coupling such that the spring is not attached to the drive member but e.g. to the number sleeve, which may entrain the dose dial member to drive the drive member during dose dispensing, if the drive member is coupled to the dose dial member.

According to a preferred embodiment, the drug delivery device comprises a limiter mechanism defining a maximum settable dose and a minimum settable dose. Typically, the minimum settable dose is zero (0 U of insulin formulation), such that the limiter stops the device at the end of dose dispensing. The maximum settable dose, for example 60, 80 or 120 U of insulin formulation, may be limited to avoid overdosage. Preferably, the limits for the minimum dose and the maximum dose are provided by hard stop features.

The limiter mechanism may comprise a first rotational stop on the number sleeve and a first counter stop on the housing or a housing insert, which abut in the minimum dose (zero) position, and a second rotational stop on the number sleeve and a second counter stop on the housing or a housing insert, which abut in the maximum dose position. As the number sleeve rotates relative to the housing during dose setting and during dose dispensing, these two components are suitable to form a reliable and robust limiter mechanism. Preferably, the counter stops are both located on the gauge window, which is an insert rotationally constrained to the housing but axially displaceable relative to the housing.

The cartridge may be located on a first longitudinal axis, which is parallel to and spaced from a second longitudinal axis, on which the drive sleeve and the dose dial member are located. Preferably, the two different display members are both located on the second longitudinal axis.

According to a further embodiment of the present invention the handheld injection device comprises a housing, a piston rod, a driver, a dose setting means, a power reservoir (e.g. a spring) and a release clutch. The piston rod defines a first longitudinal axis and is located within the housing. The driver is coupled to the piston rod. The dose setting means is rotatable about a second longitudinal axis at least during dose setting. The power reservoir drives the driver during dose dispensing. The release clutch is arranged such that it prevents rotation of the driver during dose setting and allows rotation of the driver during dose dispensing. The first longitudinal axis is parallel to and spaced from the second longitudinal axis, i.e. there is an offset between the two axes on which the component parts of the device are arranged.

Due to some of the component parts being located next to others instead of the conventional concentrically arrangement, the cross-section of the device becomes rather elongated than the usual circular pen-shape. This improves handling of the device at least for some users. Further, the device may be made shorter and less bulky, which again improves handling. Providing the power reservoir for driving the driver reduces the force required for the user during dose dispensing. This is especially helpful for users with impaired dexterity.

To improve handling of the device, the length of the device before and after dose setting is preferably the same. In other words, there is no dial extension due to components winding out of the housing during dose setting. Preferably, the dose setting means and the driver are arranged in the housing such that they are prevented from axial displacement along one of the longitudinal axes during dose setting and during dose dispensing. However, an axial movement of at least some of the components between dose setting and dose dispensing may be possible for switching between a dose setting position and a dose dispensing position of the device.

According to a further embodiment of the present invention the handheld injection device may comprise a housing containing a cartridge, a dose setting means, which is operable, e.g. rotatable, in a first direction to set a desired dose to be dispensed, a piston rod, which is adapted to cooperate with a piston or bung so as to cause a set dose to be injected from the cartridge, and first and second clicker components. The first clicker component may be rotationally constrained to the housing, whereas the second clicker component may be rotatable relative to the housing during dose dispensing. To provide a non-visual, i.e. an audible and/or tactile, first feedback to a user only at the end of dispensing of a set dose, the clicker components are adapted to contact each other. If a click activator interacting with the first clicker component is axially displaceable relative to the housing between a proximal dose setting position and a distal dose dispensing position, the first feedback is generated only if the device is in its dose dispensing mode with the click activator being in its distal dose dispensing position. However, if the device is in its dose setting mode with the click activator being in its proximal dose setting position, the two clicker components do not engage with each other, thus preventing that a signal or feedback is generated. Thus, dialing up from a minimum dose of zero, will not need to overcome the clicker arrangement because no contact occurs between the clicker components. As an example, a clicker arm on the number sleeve may be pushed radially outwards from its unstressed dose setting position into its dose dispensing position by a click activator rod having an inclined, preferably a truncated or tapered, part acting on the clicker arm if the click activator rod is moved distally together with the dose button.

A further advantage of the first clicker component which has a dose setting position and a dose dispensing position, is that the dose setting means may be operable, e.g. rotatable, in a second direction which is opposite to the first direction to cancel a set dose, without the first and second clicker components contacting each other and, thus, without creating the feedback. This avoids confusion of the users.

Preferably, the injection device further comprises at least one clicker producing an audible and/or tactile feedback during dose setting and/or during dose correction (cancelling of a set dose without dispensing) and/or during dose dispensing. An example may be a clutch plate rotating during dose setting with teeth riding over corresponding teeth of a drive member, which is during dose setting rotationally constrained to the housing, or a driver rotating during dose dispensing and interacting with a clicker arm of a component rotationally constrained to the housing, like an axially displaceable locking arm. To differentiate between these feedback signals, the first feedback (end of dose dispensing feedback), which is generated only at the end of dispensing of a set dose, is distinct from the further feedback(s). For example, a different sound may be generated.

The drug delivery device may comprise a cartridge containing a medicament. Further, a movable bung may be provided in the cartridge. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Non-limiting, exemplary embodiments of the invention will now be described with reference to the accompanying drawings, in which:

FIG. 4 shows a sectional view of the device of FIG. 1 in the dose setting state;

FIG. 7 shows a sectional view of the device of FIG. 1 in the dose dispensing state;

Figure 1:
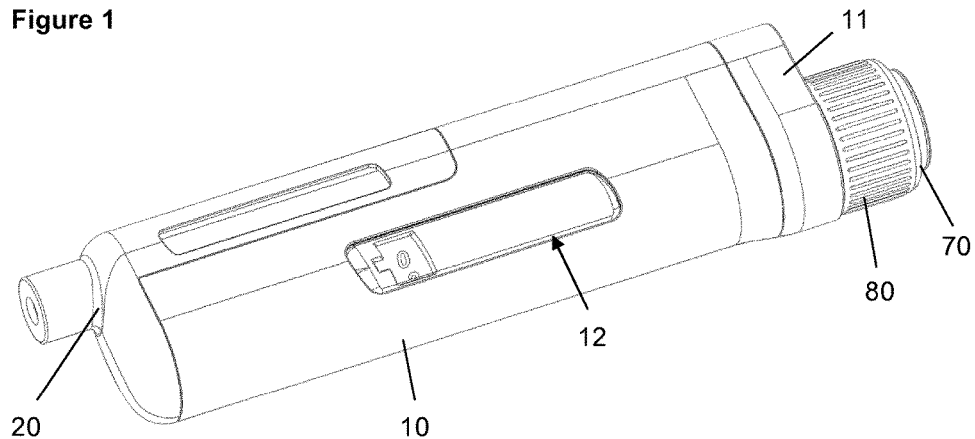
FIG. 1 shows a perspective view of an injection device in accordance with a first embodiment of the present invention.
Figure 2:
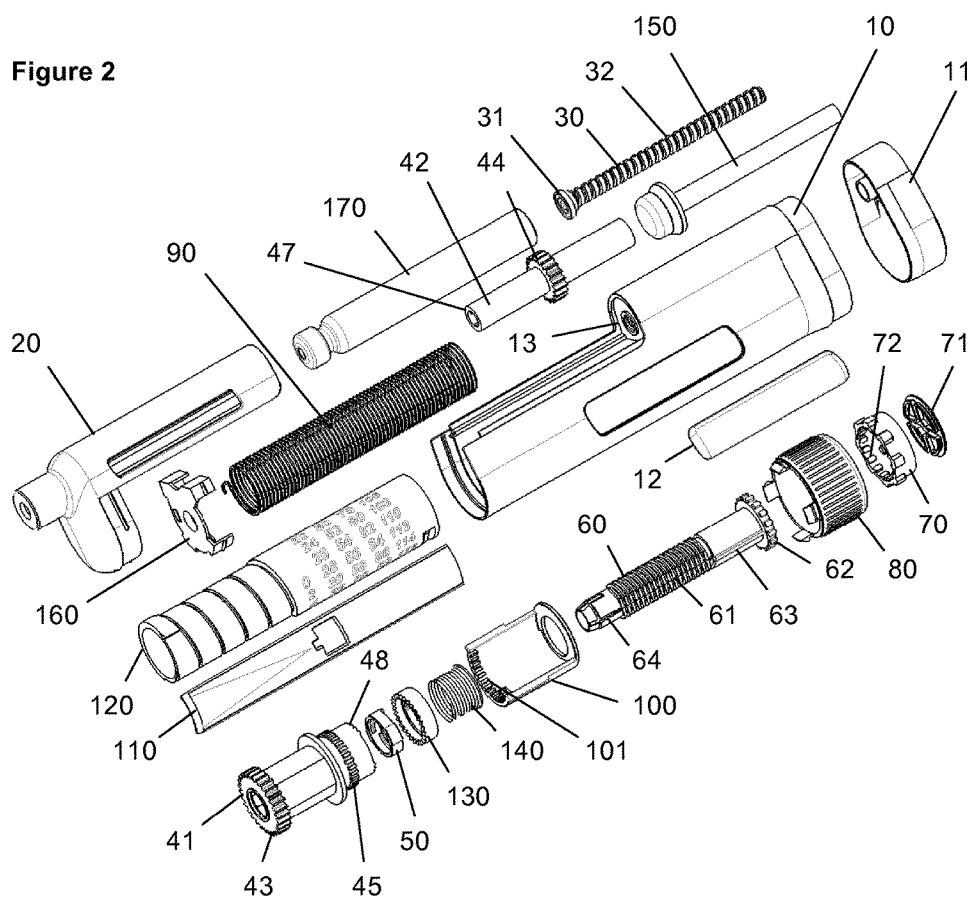
FIG. 2 shows an exploded view of the components of the device of FIG. 1.

FIG. 1 shows a drug delivery device in the form of an injection pen. The device has a distal end (lower left end in FIG. 1) and a proximal end (upper right end in FIG. 1). The component parts of the drug delivery device are shown in FIG. 2. The drug delivery device comprises a housing 10, a cartridge holder 20, a lead screw (piston rod) 30, a driver 41, 42, a nut 50, a dial sleeve 60, a button 70, a dose selector 80, a torsion spring 90, a locking arm 100, a gauge element 110, a dose indicator (number sleeve) 120, a clutch plate 130, a clutch spring 140, a click activator 150, a drive spring retainer 160 and a cartridge 170. A needle arrangement (not shown) with a needle hub and a needle cover may be provided as additional components, which can be exchanged as explained above.

The housing 10 or body is a generally tubular element with an elongate cross-section. In the embodiment shown in the figures, all components are located within the main housing 10 component, concentrically mounted about one of two, parallel axes I, II of the mechanism. A body cap 11 is snapped, press-fitted, and/or glued or welded onto the proximal end of main housing 10. Further, a lens 12 is inserted in an elongate aperture of main housing 10. The main housing 10 has a threaded inner wall 13 (web) for receiving piston rod 30. In addition, the housing 10 provides location for the liquid medicament cartridge 170 and cartridge holder 20, a housing cap (not shown), drive spring retainer 160, an interface to rotationally constrain the locking arm 100 and a feature on its external surface to axially retain the dial grip 80.

The cartridge holder 20 is the distal part of the housing and may be snapped, press-fitted, and/or glued or welded onto the distal end of main housing 10. The cartridge holder 20 receives the cartridge 170 and has a distal opening for attachment of the needle and a window or aperture allowing a user to see the cartridge.

The piston rod 30 has a bearing 31 on its distal end, which may be axially constrained to the piston rod 30 and acts on the bung within the liquid medicament cartridge 170. The piston rod 30 is a lead screw with an outer thread 32 for engagement with the threaded inner wall 13 and is rotationally constrained to the drive tube 42 via a splined interface 33. When rotated, the piston rod 30 is forced to move axially relative to the drive tube 42, through its threaded interface 13, 32 with the housing 10.

In the exemplary embodiment, the driver 40 comprises two components, a drive sleeve 41 and a drive tube 42, which are located on the offset parallel axes I, II. The drive sleeve 41 extends from an interface (proximal face teeth 48) with the dial sleeve 60 (via the clutch plate 130) to a gear toothed engagement (pinions 43, 44) to the drive tube 42, and incorporates a spline toothed interface 45 with the locking arm 100. Further, drive sleeve 41 comprises splines 46 on its inner surface for engaging nut 50. The drive tube 42 is in gear toothed engagement to the drive sleeve 41 and is splined to the piston rod 30 via splines 47 on its inner surface. The drive tube 42 is fixed axially relative to both the housing 10 and drive sleeve 41.

The last dose nut 50 is located between the dial sleeve 60 and the drive sleeve 41. It is rotationally constrained to the drive sleeve 41, via a splined interface. It moves along a helical path relative to the dial sleeve 60, via a threaded interface, when relative rotation occurs between the dial sleeve 60 and drive sleeve 41 (i.e., during dialing).

The dial sleeve 60 is a dose dial member with a tubular form having an external thread 61 engaging the nut 50, a set of clutch spline teeth 62 at its proximal end for engagement with dose button 70 and splines 63 for engagement with clutch plate 130. Further splines 64 interact with corresponding grooves of the number sleeve 120.

The dose button 70 is permanently splined to the dial grip 80 via outer teeth 72 and splined to the dial sleeve 60 when the dose button 70 is not pressed. This spline interface with the dial sleeve 60 is disconnected when the dose button 70 is pressed.

The dial grip 80 is axially, but not rotationally constrained to the housing 10. It is rotationally constrained, via the splined interface, to the dose button.

The drive spring 90 is attached at one end to the drive spring retainer 160 (which forms part of the housing with the main housing 10) and at the other end to the number sleeve 120. The drive spring 90 is a torsion spring pre-wound upon assembly, such that it applies a torque to the number sleeve 120 when the mechanism is at zero units dialed. The action of rotating the dial grip 80, to set a dose, rotates the number sleeve 120 relative to the housing 10, and further charges the drive spring 90.

The locking arm 100 is rotationally fixed to the housing 10 but allowed to translate axially. When the dose button 70 is pressed, the locking arm 100 spline teeth 101 are disengaged from the drive sleeve 41 allowing the drive sleeve 41 to rotate.

The gauge element 110 is constrained to prevent rotation, but allow axial translation relative to the housing 10 via a splined interface. It is also in threaded engagement to the number sleeve 120 such that rotation of the number sleeve 120 causes axial translation of the gauge element 110. A window 111 is provided in the gauge element with a distal part and a proximal part of the gauge element extending in the respective directions of the window. The outer surface of these parts has a different design, for example in the embodiment of FIG. 2 a triangle is printed on the distal part.

The number sleeve 120 is rotationally constrained, via a splined interface, to the dial sleeve 60. Both components are constrained to the housing 10 to allow rotation, but not translation. The number sleeve 120 is marked with a sequence of numbers, which are visible through the gauge element 110 and a lens 12, located in a slot in the housing 10, to denote the dialed dose of medicament. A zero dose abutment feature 121 and a maximum dose abutment feature 122 are provided as rotational hard stops. Further, there is an end of dose clicker arm 123 at the distal end of number sleeve 120.

The clutch plate 130 is splined to the dial sleeve 60. It is also coupled to the drive sleeve 41 via a ratchet interface (via teeth 131), which occurs on an axial abutment. The ratchet provides a detented position between the dial sleeve 60 and drive sleeve 41 corresponding to each dose unit, and engages different ramped tooth angles during clockwise and anticlockwise relative rotation.

The clutch spring 140 acts between the clutch plate 130 and the locking arm 100 to force the spline teeth into engagement with the drive sleeve 41 and to force the ratchet between the clutch plate 130 and the drive sleeve 41 together. The axial position of the locking arm 100, clutch plate 130 and dose button 70 are defined by the action of the clutch spring 140. In the "at rest" position, this ensures that the dose button 70 splines are engaged with the dial sleeve 60 and that the drive sleeve 41 spline teeth are engaged with the locking arm 100.

The click activator 150 is axially constrained to the button cap 71 and moves the end of dose clicker arm outwards radially when the dose button 70 is depressed.

The drive spring retainer 160 is held within housing 10 and receives the distal end of drive spring 90. In the embodiment of FIG. 2 the retainer is shown as a separate component part, however, the retainer may as well be an integral part of the housing 10.

The removable cap (not shown) fits over the cartridge holder 20 and housing 10 components and is retained via clip features.

In the following, the functioning of the disposable drug delivery device and its components will be explained in more detail.

With the device in the 'At Rest' condition, the zero dose abutment feature 121 of the number sleeve 120 is positioned against a corresponding zero dose abutment stop of the gauge element 110 (see FIG. 3) and the dose button 70 is not depressed. Dose marking '0' on the number sleeve 120 is visible through the window (lens 12) of the housing 10 and window 111 of gauge element 110. The drive spring 90, which has a number of pre-wound turns applied to it during assembly of the device, applies a torque to the number sleeve 120 and is prevented from rotating further by the zero dose abutment. It is also possible to "back-wind" the mechanism slightly due to an offset between the zero dose stop and the angular offset of the drive sleeve 41 spline teeth. This has the effect of preventing possible weeping of medicament when a dose is dialed and the zero dose abutment is disengaged.

Figure 5:
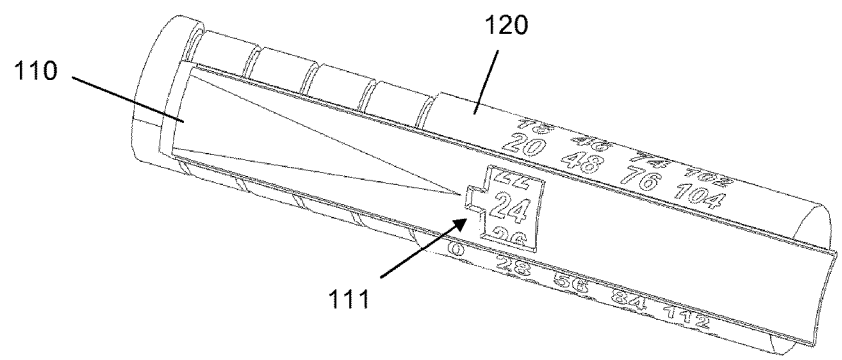
FIG. 5 shows an enlarged view of components of the device of FIG. 1.

The user selects a variable dose of liquid medicament by rotating the dial grip 80 clockwise, which generates an identical rotation in the dial sleeve 60 and hence number sleeve 120. Rotation of the number sleeve 120 causes charging of the drive spring 90, increasing the energy stored within it. As the number sleeve 120 rotates, the gauge element 110 translates axially due to its threaded engagement thereby showing the value of the dialed dose. The gauge element 110 has flanges either side of the window area which may have visual differentiation to provide additional feedback as to the dialed/delivered dose value (shown in FIG. 5) and which obscure those numbers that would be visible in the body slot that do not correspond to the dialed dose display. The dial grip 80 has an increased diameter relative to the housing 10 which aids dialing. This is especially important for an auto-injector mechanism where the stored energy source is charged during dose setting.

The drive sleeve 41 is prevented from rotating, due to the engagement of its splined teeth with the locking arm 100. Relative rotation must therefore occur between the clutch plate 130 and drive sleeve 41 via the dialing ratchet interface.

The user torque required to rotate the dial grip 80 is a sum of the torque required to wind up the drive spring 90, and the torque required to overhaul the dialing ratchet feature. The clutch spring 140 is designed to provide an axial force to the ratchet feature and to bias the clutch plate 130 against the drive sleeve 41. This axial load acts to maintain the ratchet teeth engagement (teeth 48 and 131) of the clutch plate 130 and drive sleeve 41. The torque required to overhaul the ratchet is resultant from the axial load applied by the clutch spring 140, the clockwise ramp angle of the ratchet, the friction coefficient between the mating surfaces and the mean radius of the ratchet features.

As the user rotates the dial grip 80 sufficiently to increment the mechanism by one unit, the dial sleeve 60 rotates relative to the drive sleeve 41 by one ratchet tooth. At this point the ratchet teeth 48, 131 re-engage into the next detented position. An audible click is generated by the ratchet re-engagement, and tactile feedback is given by the change in torque input required.

Relative rotation of the dial sleeve 60 and the drive sleeve 41 also causes the last dose nut 50 to travel along its threaded path, towards its last dose abutment on the dial sleeve 60.

With no user torque applied to the dial grip 80, the dial sleeve 60 is now prevented from rotating due to the action of the torque applied by the drive spring 90, solely by the ratchet engagement (teeth 48, 131) between the clutch plate 130 and the drive sleeve 41. The torque necessary to overhaul the ratchet in the anti-clockwise direction is resultant from the axial load applied by the clutch spring 140, the anti-clockwise ramp angle of the ratchet, the friction coefficient between the mating surfaces and the mean radius of the ratchet features. The torque necessary to overhaul the ratchet must be greater than the torque applied to the dial sleeve 60 (and hence clutch plate 130) by the drive spring 90. The ratchet ramp angle is therefore increased in the anti-clockwise direction to ensure this is the case whilst ensuring the dial-up torque is as low as possible.

The user may now choose to increase the selected dose by continuing to rotate the dial grip 80 in the clockwise direction. The process of overhauling the ratchet interfaces between the dial sleeve 60 and drive sleeve 41 is repeated for each dose unit. Additional energy is stored within the drive spring 90 for each dose unit and audible and tactile feedback is provided for each unit dialed by the re-engagement of the ratchet teeth. The torque required to rotate the dial grip 80 increases as the torque required to wind up the drive spring 90 increases. The torque required to overhaul the ratchet in the anti-clockwise direction must therefore be greater than the torque applied to the dial sleeve 60 by the drive spring 90 when the maximum dose has been reached.

If the user continues to increase the selected dose until the maximum dose limit is reached, the number sleeve 120 engages with its maximum dose abutment 122 on the gauge element 110, which prevents further rotation of the number sleeve 120, dial sleeve 60, clutch plate 130 and dial grip 80.

Depending on how many units have already been delivered by the mechanism, during selection of a dose, the last dose nut 50 may contact its last dose abutment with the dial sleeve 60, which is shown in FIG. 7 as a landing on dial sleeve 60 between threads 61 and splines 63. The abutment prevents further relative rotation of the dial sleeve 60 and the drive sleeve 41, and therefore limits the dose size that can be selected. The position of the last dose nut 50 is determined by the total number of relative rotations between the dial sleeve 60 and drive sleeve 41, which have occurred each time the user sets a dose.

With the mechanism in a state in which a dose has been selected, the user is able to deselect any number of units from this dose. Deselecting a dose is achieved by the user rotating the dial grip 80 anti-clockwise.

The torque applied by the drive spring 90 on the mechanism is in the anti-clockwise direction, therefore the torque required from the user on the dial grip 80 to deselect a dose is that to overhaul the ratchet between the clutch plate 130 and drive sleeve 41 in the anti-clockwise direction less the drive spring 90 torque at that particular number sleeve 120 rotational position.

When the ratchet is overhauled, anti-clockwise rotation occurs in the dial sleeve 60 (via the clutch plate 130), which returns the number sleeve 120 towards the zero dose position, and unwinds the drive spring 90. The relative rotation between the dial sleeve 60 and drive sleeve 41 causes the last dose nut 50 to return along its helical path, away from the last dose abutment on the dial sleeve 60.

With the mechanism in a state in which a dose has been selected, the user is able to activate the mechanism to commence delivery of a dose. Delivery of a dose is initiated by the user depressing the dose button 70 on the top of the device.

Figure 3:
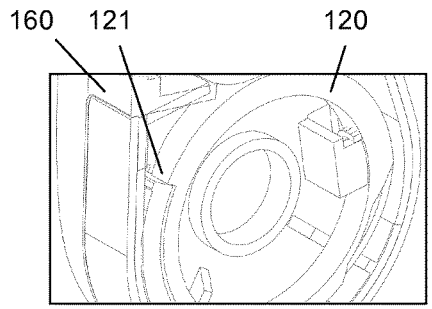
FIG. 3 shows an enlarged view of a detail of the device of FIG. 1.
Figure 6:
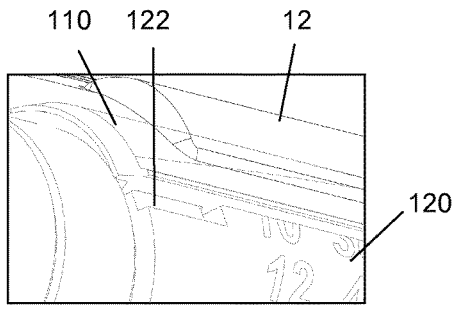
FIG. 6 shows an enlarged view of a detail of the device of FIG. 1.

When the dose button 70 is depressed, its splined engagement with the dial sleeve 60 is disengaged, rotationally disconnecting the dose button 70 and hence dial grip 80 from the delivery mechanism so that the dial grip 80 does not rotate during dispense. The dose button 70 acts on the locking arm 100, which travels axially disconnecting the splined tooth engagement to the drive sleeve 41. The drive sleeve 41 can now rotate and is driven by the drive spring 90 via the number sleeve 120, dial sleeve 60 and clutch plate 130. Rotation of the drive sleeve 41 causes the drive tube 42 to rotate, which in turn causes the piston rod 30 to rotate due to their splined engagement. The piston rod 30 then advances due to its threaded engagement to the housing 10. The number sleeve 120 rotation also causes the gauge element 110 to traverse axially back to its zero position whereby the zero dose abutment stops the mechanism as shown in FIG. 3.

Audible feedback during delivery is provided via a compliant cantilever dispense clicker arm 102 integrated into the locking arm 100, which interfaces axially with the spline teeth 45 of the drive sleeve 41. The spline teeth spacing corresponds to the drive sleeve 41 rotation required for a single dispense unit. During dispense, as the drive sleeve 41 rotates, the spline features 45 engage with the dispense clicker arm 102 to produce an audible click with each dose unit delivered.

Delivery of a dose continues via the mechanical interactions described above while the user continues to depress the dose button 70. If the user releases the dose button 70, the clutch spring 140 returns the dose button 70 to its 'at rest' position via the locking arm 100 and clutch plate 130, the drive sleeve 41 and hence drive tube 42 become rotationally constrained, and delivery of a dose is halted.

During delivery of a dose, the drive sleeve 41 and dial sleeve 60 rotate together, so that no relative motion in the last dose nut 50 occurs. The last dose nut 50 therefore travels towards its abutment on the dial sleeve 60 during dialing only.

Once the delivery of a dose is stopped by the number sleeve 120 returning to the zero dose abutment, the user may release the dose button 70, which will re-engage the locking arm 100 spline teeth 101 with teeth 45 of the drive sleeve 41. The mechanism is now returned to the 'at rest' condition.

It is possible to angle the spline teeth 45, 101 on either the drive sleeve 41 and/or the locking arm 100 so that when the dose button 70 is released the re-engagement of the spline teeth fractionally 'backwinds' the drive sleeve 41 thereby removing the engagement of the number sleeve 120 to the gauge element 110 zero dose stop abutment. This removes the effect of clearances in the mechanism (for example due to tolerances) which could otherwise lead to slight advancement of the piston rod 30 and medicament dispense when the device is dialed for the subsequent dose (due to the number sleeve 120 zero dose stop no longer restraining the mechanism and instead the restraint returning to the splines between the drive sleeve 41 and gauge element 110).

At the end of dose, additional audible feedback is provided in the form of a click (distinct from the dispense clicks) that informs the user that the dispense mechanism has returned to the zero position via the interaction of three components: number sleeve 120, gauge element 110 and click activator 150. The embodiment allows feedback to only be produced at the end of dose delivery (when the dose button 70 is depressed) and not when the device is being dialed into, or away from, the zero position.

Figure 8A:
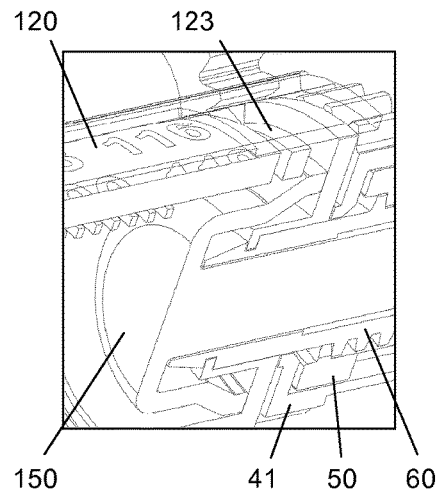
FIG. 8a shows an enlarged view of a detail of the device of FIG. 1 in the dose setting state.
Figure 8B:
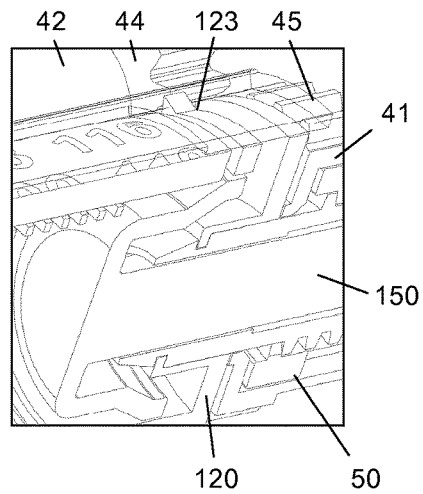
FIG. 8b shows an enlarged view of a detail of the device of FIG. 1 in the dose dispensing state.
Figure 9A:
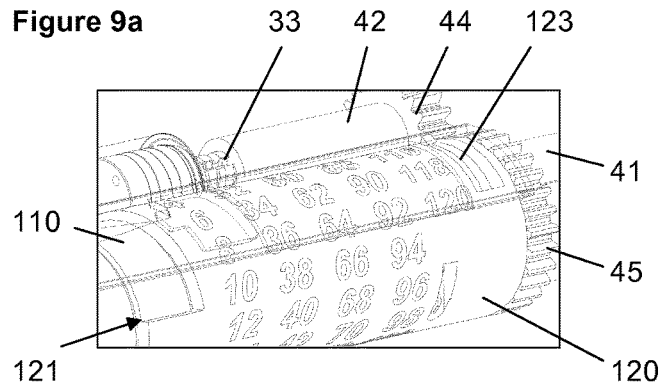
FIG. 9a shows an enlarged view of a detail of the device of FIG. 1.
Figure 9B:
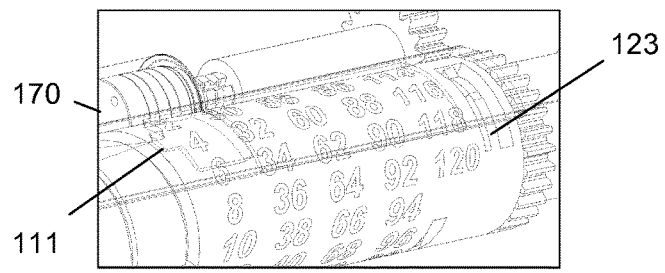
FIG. 9b shows an enlarged view of a detail of the device of FIG. 1.
Figure 9C:
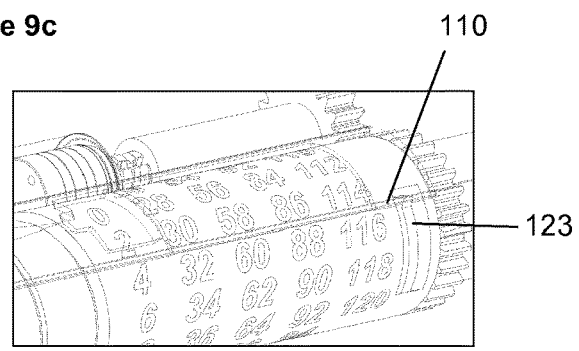
FIG. 9c shows an enlarged view of a detail of the device of FIG. 1.
Figure 9D:
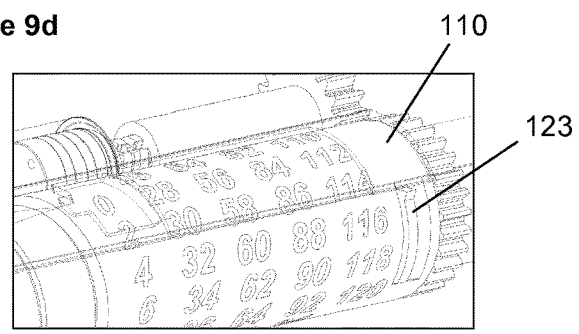
FIG. 9d shows an enlarged view of a detail of the device of FIG. 1.

When the dose button 70 is not depressed (i.e. during dialing), the end of dose clicker arm 123 is sub-flush with the number sleeve 120 outer surface, and so is clear of the gauge element 110 as the device is dialed into, or away from, the zero position, hence no end of dose click can be produced. This is shown in FIG. 8a. When the dose button 70 is depressed (i.e. during dispense), the click activator 150 is moved axially so that it forces the end of dose clicker arm 123 radially outwards as shown in FIG. 8b.

The function of the zero dose click is further shown in FIGS. 9a to 9d which depict the sequence of dispensing from 6 units set down to zero. Usually, the gauge element 110 would conceal the number sleeve 120 and its arm 123 at least partly. However, in FIGS. 9a to 9d the gauge element 110 is shown transparent. As the number sleeve 120 rotates towards the zero position during dispense, the deflected end of dose clicker arm 123 contacts the gauge element 110 at around six units (see FIG. 9a). This causes a preload to be generated in the clicker arm 123 in the radial direction (see FIG. 9b). The drive spring 90 is sufficiently strong to overcome the additional friction caused by the interference between gauge element 110 and the end of dose clicker arm 123 tip. This preload is maintained as the tip of the end of dose clicker arm 123 is in contact with the gauge element 110 up to a point just prior to zero unit position (see FIG. 9c). At this point the tip of the end of dose clicker arm 123 slides off a feature (not shown) formed locally at the trailing edge of the gauge element 110, producing an audible "click" (see FIG. 9d).

As the dose button 70 needs to be released before the device can be dialed away from the zero unit position, the end of dose clicker arm 123 moves inwards radially as the click activator 150 moves rearwards with the dose button 70 and therefore it cannot interfere with the gauge element 110 during dialing. This ensures the end of dose click is only produced between one and zero units and only during dispense.

Independent from the above detailed embodiment, the invention relates to a mechanism for use in a medical device that can be operated to deliver variable, user-selectable, doses of medicament from a cartridge, e.g. via a needle. The device is preferably disposable. It is delivered to the user in a fully assembled condition ready for first use.

The mechanism provides separate user interfaces for setting and delivery of a dose. A dose is set by rotating a dial grip 80 located at the end of the housing 10. Delivery of a dose is initiated by pressing a dose button 70 on the end of the dial grip 80. Dose delivery will continue while the dose button 70 remains depressed, until the complete set dose has been delivered. The mechanism provides audible, visual and tactile feedback both on the setting and delivery of each dose.

The mechanism contains a helical drive spring 90 to store energy, which is charged during setting of the dose, by the action of the user rotating the dial grip 80. The spring energy is stored until the mechanism is triggered for dispense at which point the energy stored is used to deliver the medicament from the cartridge to the user.

Any dose size can be selected between zero and a predefined maximum, in increments to suit the medicament and user profile. The mechanism permits cancelling of a dose without any medicament being dispensed by rotation of the dial grip 80 in the opposing direction to when selecting a dose.

Figure 10:
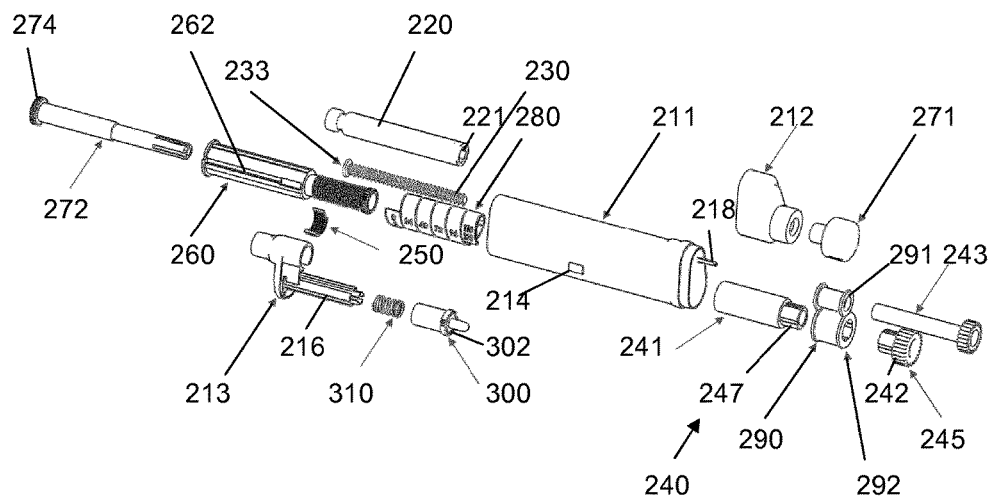
FIG. 10 shows an exploded view of an injection device in accordance with a second embodiment of the present invention.
Figure 11:
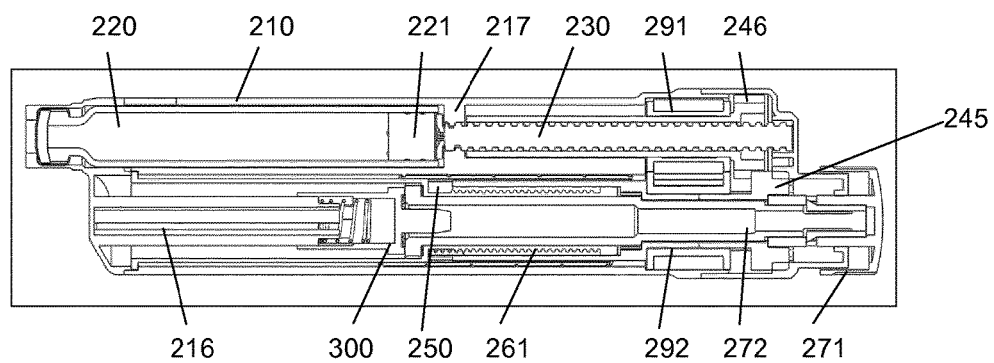
FIG. 11 shows a sectional view of the device of FIG. 10 in the dose setting state.
Figure 12:
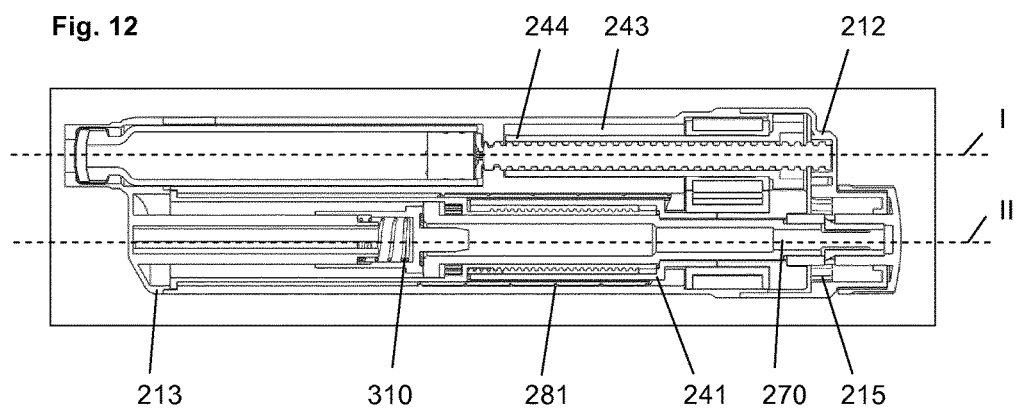
FIG. 12 shows a sectional view of the device of FIG. 10 in the dose dispensing state.

FIGS. 10 to 12 show a second embodiment of the invention, which differs from the first embodiment amongst others in the design of the spring and in the way the dose is displayed.

The device has a distal end (left end in FIG. 11) and a proximal end (right end in FIG. 11). The component parts of the drug delivery device are shown in FIG. 10. The drug delivery device comprises a housing 210, a cartridge 220, a lead screw (piston rod) 230, a driver 240, a nut 250, a dial sleeve 260, a dial assembly 270, a number sleeve 280, a power reservoir (motor spring) 290, a clicker 300 and a spring 310. A needle arrangement (not shown) with a needle hub and a needle cover may be provided as additional components, which can be exchanged as explained above.

The housing 210 or body comprises a main housing 211, a proximal housing 212 and a distal housing or cartridge holder 213. The main housing 211 is a generally tubular element with an oblong cross section with the lower side in FIG. 11 being widened compared with the upper side. A window 214 or aperture is provided in the main housing 211. The main housing 211, the proximal housing 212 and the cartridge holder 213 can be plugged or snapped together during assembly to close both open ends of the main housing 211. Further, the housing components may be glued or welded together to form a rigid and permanently attached housing unit. The proximal housing 212 has a proximal aperture in its lower region in FIG. 10, and the cartridge holder 213 has a distal aperture in its upper region in FIG. 10, which may have an outer thread or the like for attachment of a needle arrangement. Further, the proximal housing 212 has on its inside near the proximal aperture a ring of teeth which forms part of a clutch with driver 240. The cartridge holder 213 has on its lower side a splined pin 216 for guiding clicker 300 and spring 310. The housing 210 provides location for the liquid medication cartridge 220, which is held in the upper part (as seen in FIG. 10) of the main housing 211 and the cartridge holder 213.

The main housing has an inner wall with a threaded section 217 engaging piston rod 230. Further, there is a clicker arm 218 near the proximal end of main housing 211, which arm interacts with the driver 240 during dose dispensing.

The cartridge 220 is a glass ampoule with a movable rubber bung 221 located in its proximal aperture.

The lead screw 230 is an elongate member with an outer thread which is rotationally constrained to the driver 240 via a splined interface. The interface comprises at least one longitudinal groove or track and a corresponding protrusion or spline of the driver 240. When rotated, the lead screw 230 is forced to move axially relative to the driver 240, through its threaded interface 217 with the housing 210. The distal end of the piston rod 230 is provided with a bearing 233, which may abut the cartridge bung 221.

The driver 240 comprises a drive sleeve, which has for manufacturing reasons a drive sleeve lower part 241 and a drive sleeve upper part 242, and a drive tube 243. The drive sleeve lower part 241 and the drive sleeve upper part 242 are rigidly connected to form a unit when in use. The drive tube 243 is arranged on a first longitudinal axis I and the drive sleeve is arranged on a second longitudinal axis II, which is parallel to and spaced from the first axis I.

On the inside of the drive tube 243, splines 244 are provided engaging corresponding grooves of the piston rod 230. The drive tube 243 surrounds the piston rod 230 which is axially displaceable relative to the drive tube 243. As shown in FIGS. 11 and 12, the drive sleeve upper part 242 and the drive tube 243 each have at their proximal end a pinion 245, 246, which mesh such that rotation of the drive sleeve is transmitted to the drive tube. The drive sleeve is axially movable along the second axis II between a proximal position (during dose setting and correcting, see FIG. 11) in which pinion 245 further engages teeth 215 of the housing 210, and a distal (dose dispensing position, see FIG. 12) in which the pinion 245 is disengaged from the teeth 215. However, in both axial positions pinions 245, 246 remain into engagement.

The drive sleeve has on its outer surface splines 247 for rotationally constraining the drive sleeve to the power reservoir 290. Further, splines are provided on the inner surface of the drive sleeve for rotationally constraining the drive sleeve to nut 250.

The nut 250 is part of a last dose limiter mechanism. The last dose nut 250 is located between the dial sleeve 260 and the drive sleeve 241, 242. It moves along a helical path relative to the dial sleeve 260, via a threaded interface 261, when relative rotation occurs between the dial sleeve 260 and drive sleeve during dialing, i.e. during dose setting or dose correcting. In the embodiment of FIGS. 10 to 12, the nut 250 is a half nut, i.e. a component extending approximately 180° around the second axis II of the device.

The dial sleeve 260 is a tubular element arranged rotatable on the second axis II. A proximal section of the dial sleeve 260 is provided with a thread 261 guiding the nut 250. An adjacent distal section is provided with outer splines 262 for engagement with the number sleeve 280. Further, the dial sleeve 260 has a ring of inner teeth at an intermediate stepped portion for releasably rotationally coupling the dial sleeve 260 to the dial assembly 270.

The dial assembly 270 comprises dial grip 271 and a tubular element 272 which is rigidly attached to the dial grip 271. The dial grip 271 and the tubular element 272 are in the present embodiment separate components for manufacturing reasons but may also be a single component. The dial assembly 270 is arranged on the second axis II and extends through the proximal aperture in the proximal housing part 212. At its distal end, the dial assembly is provided with a ring of teeth on its distal face for interaction with clicker 300. Further, a pinion 274 is provided near the distal end of tubular element 272 engaging teeth of dial sleeve 260 in the dose setting position. The dial assembly 270 is axially movable along the second axis II between a proximal position (during dose setting and correcting, see FIG. 11) and a distal (dose dispensing position, see FIG. 12). The dial grip 271 abuts the drive sleeve such that axial movement of the dial grip in the distal direction entrains the drive sleeve and axial movement of the drive sleeve in the proximal direction entrains the dial grip.

The number sleeve 280 is a tubular element arranged on the second axis II. The outer surface of the number sleeve 280 is provided with a sequence of numbers arranged on a helical path. Further, the number sleeve has on its outer surface a thread 281 engaging a corresponding thread of the main housing 211. At its distal end, the number sleeve 280 is provided with an inwardly directed protrusion for interaction with the dial sleeve 260. Further, there are rotational hard stops on the number sleeve 280 and corresponding elements on the main housing 211 limiting the rotational movement of the number sleeve relative to the housing on its helical path defined by the threaded interface.

The power reservoir comprises a reverse wound flat spiral spring 290, that is a band-like spring, which has a spiral form in its unstressed condition and is wound counter to that unstressed spiral direction for tensioning the spring. A first end of the spring 290 is attached to a first spool 291, which is located on the first longitudinal axis I surrounding drive tube 243. A second end of the spring 290 is attached to a second spool 292, which is located on the second longitudinal axis II and is rotationally constrained to the drive sleeve by splines 247 and corresponding grooves inside the second spool 292. Spring 290 is fully charged (tensioned) during assembly of the device by winding the spring on spool 292, whereas the spring tends to wind back on spool 291. The power reservoir is dimensioned such that spring 290 is able to drive the piston rod 230 from its retracted position shown in FIGS. 11 and 12 to a position, where the cartridge bung is pushed in its most distal direction. In other words, recharging of the spring 290 is not necessary for emptying cartridge 220.

The clicker 300 is a tubular element positioned axially displaceable but rotationally constrained on splined pin 216 of the cartridge holder 213. The clicker 300 has grooves on its inner surface for engagement with the splined pin 216. Further, there are clicker teeth 302 on the proximal end of clicker 300 mating with teeth of the dial assembly. A finger, which interacts with protrusion of the number sleeve, is provided near the teeth 302.

Spring 310 is a compression spring located on splined pin 216 and inside clicker 300 urging clicker 300 in the proximal direction. Due to the contact between the clicker 300 and the dial assembly 270 and due to the contact between the dial assembly 270 and the drive sleeve, the spring pushes these components in the proximal direction as shown in FIG. 11, whereas a user may overcome the spring 310 force and push these components in the distal position shown in FIG. 12.

During dose setting, the nut 250 advances towards a rotational abutment at the proximal end of the dial sleeve 260 whilst there is relative rotation between the dial sleeve 260 and drive sleeve 241, 242. When the abutment is reached, dial torque is reacted through the dial grip 271, dial sleeve 260, nut 250 and drive sleeve 241, 242 back to the splined interface with the housing 210. As the dial sleeve 260 and the drive sleeve 241, 242 both rotate during dose dispensing, the nut 250 maintains its position on the dial sleeve 260.

Although not shown in the embodiment of FIGS. 10 to 12, a gauge element as described above may be included in this device in addition to the number sleeve 280.

The invention claimed is:

1. An injection device comprising:
    a housing containing a cartridge with an amount of liquid to be dispensed;
    a drive sleeve which is rotationally constrained to the housing during dose setting and rotatable by a torsion spring relative to the housing during dose dispensing;
    a dose dial member to set a dose to be dispensed, which is rotatable relative to the housing during dose setting and during dose dispensing, and which is rotationally coupled to the drive sleeve during dose dispensing;
    a last dose protection mechanism to prevent the setting of a dose which exceeds the amount of liquid left in a cartridge, the last dose protection mechanism comprising a limiter, which is interposed between the drive sleeve and the dose dial member; and a display member to indicate the set dose, wherein during dose dispensing the drive sleeve is coupled to the torsion spring, which is strained during dose setting, wherein the cartridge is located on a first longitudinal axis (I), which is parallel to and spaced from the second longitudinal axis (II), on which the drive sleeve and the dose dial member are located.

2. The injection device according to claim 1, wherein the housing has a first aperture or window, wherein the display member comprises:
- a dose indicator which is positioned within the housing and rotatable relative to the housing during dose setting and during dose dispensing, and
- a gauge element which is interposed between the housing and the dose indicator, and which is axially guided within the housing and in threaded engagement with the dose indicator such that rotation of the dose indicator causes an axial displacement of the gauge element, the gauge element comprising a second aperture or window, wherein the second aperture or window is positioned with respect to the first aperture or window of the housing such that at least a part of the dose indicator is visible through the first and second apertures or windows.

3. The injection device according to claim 2, wherein the dose dial member is permanently rotationally constrained to the dose indicator.

4. The injection device according to claim 2, wherein the dose indicator is a number sleeve having a series of numbers or symbols arranged on a helical line on its outer surface, and wherein the gauge element has a distal part located on the distal side of the second aperture or window and a proximal part located on the proximal side of the second aperture or window, with the distal part and the proximal part having a different outer surface.

5. The injection device according to claim 1, wherein the last dose protection mechanism comprises a nut member as the limiter, which is rotationally constrained to the drive sleeve and in threaded engagement with the dose dial member.

6. The injection device according to claim 1, wherein the limiter comprises a rotational stop and the dose dial member comprises a corresponding counter stop, which abut if a dose is set, which exceeds the amount of liquid left in a cartridge.

7. The injection device according to claim 1, further comprising a piston rod coupled to the drive sleeve, which piston rod is rotationally constrained to the housing during dose setting and is allowed to rotate during dose dispensing.

8. The injection device according to claim 1, further comprising a ratchet clutch, which is arranged between the drive sleeve and the dose dial member, and which allows relative rotation of the drive sleeve and the dose dial member during dose setting and which rotationally constrains the drive sleeve to the dose dial member during dose dispensing.

9. The injection device according to claim 1, comprising a limiter mechanism defining a maximum settable dose and a minimum settable dose.

10. The injection device according to claim 1, wherein the two different display members are located on the second longitudinal axis (II).

11. The injection device according to claim 1, wherein the length of the device before and after dose setting is the same.

12. The injection device according to claim 1, further comprising at least one first clicker producing at least one of an audible or tactile first feedback during at least one of dose setting or dose dispensing and a second clicker producing at least one of an audible or tactile second feedback, distinct from the first feedback, during dose dispensing when a minimum dose position of the device is reached.

13. The injection device according to claim 1, wherein the cartridge contains a medicament.

* * * * *